United States Patent [19]
Gewirtz et al.

[11] Patent Number: 5,427,916
[45] Date of Patent: Jun. 27, 1995

[54] METHOD FOR PREDICTING THE EFFECTIVENESS OF ANTINEOPLASTIC THERAPY IN INDIVIDUAL PATIENTS

[75] Inventors: Alan M. Gewirtz; Bruno Calabretta, both of Philadelphia, Pa.

[73] Assignee: Temple University of the Commonwealth System of Higher Education, Philadelphia, Pa.

[21] Appl. No.: 288,151

[22] Filed: Aug. 10, 1994

Related U.S. Application Data

[63] Continuation of Ser. No. 927,253, Aug. 7, 1992, abandoned, which is a continuation of Ser. No. 191,449, May 9, 1988, abandoned.

[51] Int. Cl.⁶ .................. C12Q 1/68; C07H 21/02; A61K 43/00; A61K 49/00
[52] U.S. Cl. ...................... 435/6; 536/23.1; 436/813
[58] Field of Search ........................ 536/23.1

[56] References Cited
FOREIGN PATENT DOCUMENTS
2187283 9/1987 United Kingdom.

OTHER PUBLICATIONS
Tonini et al., *Cancer Research* 47, 4544–4547 (Sep. 1, 1987).
Calabretta et al., *Proc. Natl. Acad. Sci. USA* 82, 4463–4467 (Jul. 1985).
Kelly et al., *Cell* 35, 603–610 (Dec. 1983).
Preisler et al., *J. Cell. Biochem., Suppl.* 11A, Abstract #D510, p. 237 (1987).
Preisler et al., *Cancer Res.* 47:874–880 (1987).

*Primary Examiner*—Mindy B. Fleisher
*Attorney, Agent, or Firm*—Seidel Gonda Lavorgna & Monaco

[57] ABSTRACT

The effectiveness of selected antineoplastic agents may be determined in individual patients by comparing the level of expression of one or more selected growth-regulated genes in neoplastic cells taken from the patient before and shortly after the initiation of therapy. A decrement in expression is prognostic of eventual remission, while a lack of decrement indicates that remission is unlikely. The test may also be accomplished by comparing the level of expression of growth-regulated genes in neoplastic cells in culture before and after incubation of the cells with the selected antineoplastic agents.

22 Claims, 2 Drawing Sheets

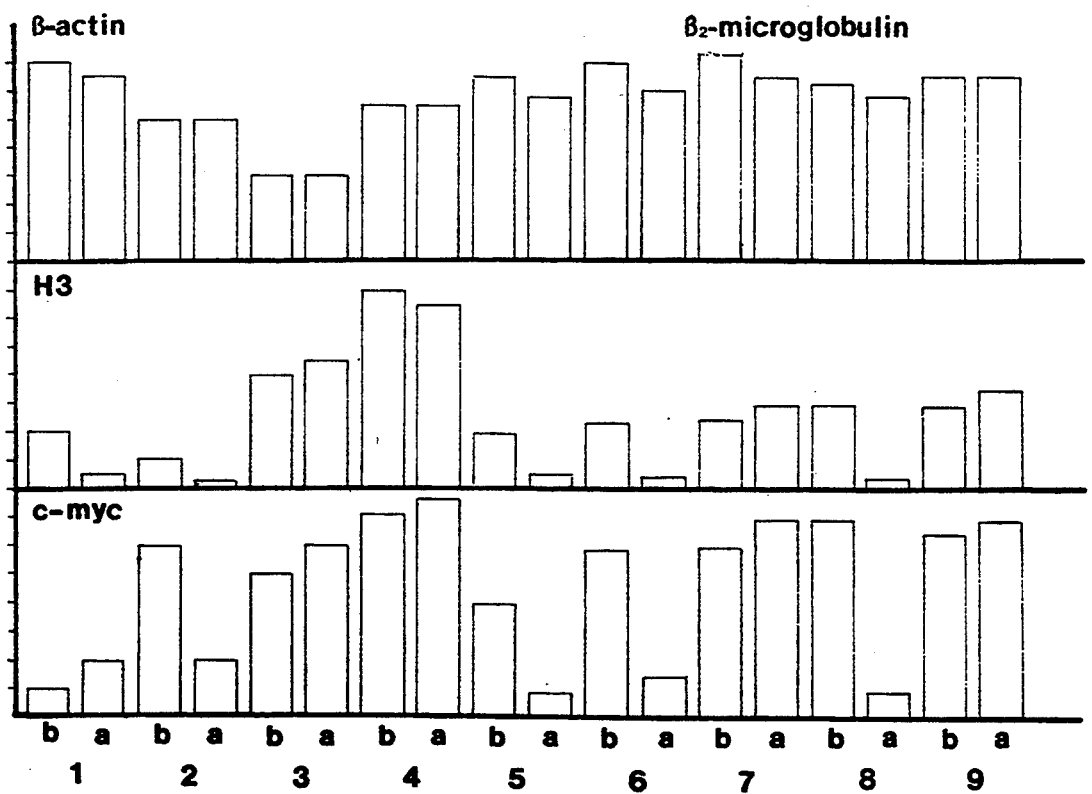
-FIG 1

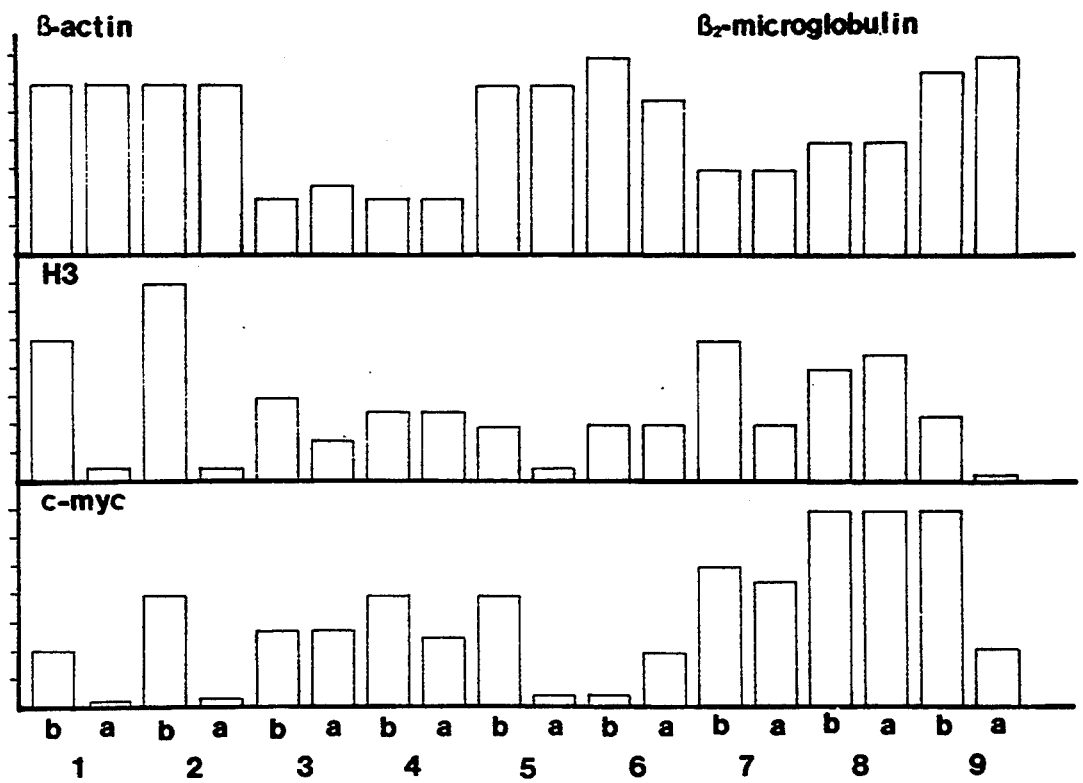
-FIG 2

METHOD FOR PREDICTING THE EFFECTIVENESS OF ANTINEOPLASTIC THERAPY IN INDIVIDUAL PATIENTS

REFERENCE TO GOVERNMENT GRANT

The invention described herein was supported in part by National Institutes of Health Grant R01 CA 36896.

This is a continuation of application Ser. No. 07/191,449 filed on May 9, 1988, now abandoned.

FIELD OF THE INVENTION

The invention relates to predicting the effectiveness of one or more selected antineoplastic agents prior to, or early in, a course of chemotherapy.

BACKGROUND OF THE INVENTION

Methods of treating cancer include radiation therapy, surgery and chemotherapy. While chemotherapy has been widely employed, the indicated chemotherapeutic agents or combinations thereof are not always successful in achieving remission. All too often, an indicated course of chemotherapy is initiated, only to result in a failure to achieve remission of the cancer. The chemotherapy may continue for weeks or even months before the physician may conclude that the treatment is unsuccessful, and that alternative chemotherapeutic agents are warranted. Valuable time is lost during the period of ineffective chemotherapy.

Clonogenic assays of tumor cells have been proposed as in vitro methods by which anticancer drugs can be selected for activity against tumor cells from a patient. The human tumor clonogenic assay of Hamburger and Salmon, Science 197:461–463 (1977), has been proposed as a test to predict clinical response or resistance. Jones et al., J. Clin. Oncol. 3:92–97 (1985). Such methods are analogous to sensitivity testing for antibiotics in patients with bacterial infections, relying on cell survival as predictive of a response to chemotherapy. However, these methods are unreliable. Selby et al., N. Engl. J. Med. 308:129–134 (1983).

In a retrospective study, Preisler et al., J. Cell. Biochem., Suppl. 11A, Abstract #D510, p.237 (1987), noted a correlation between expression of the proto-oncogenes c-myc and histone H3 and chemotherapy-induced remission in leukemia patients. In another retrospective study, it was observed that levels of c-myc RNA from bone marrow cells of acute myelocytic leukemia patients were higher than cells from another group of patients in complete remission. Preisler et al., Cancer Res. 47:874–880 (1987). Such retrospective correlations in growth-regulated gene expression following prolonged chemotherapy are attributable to neoplastic cell death and a generalized reduction of cellular mRNA, rather than drug-specific variations in growth-regulated gene expression.

Clearly, what is needed is a method for determining the probable effectiveness of a particular chemotherapeutic agent or combination of agents on an individual patient basis in advance of, or very shortly after the initiation of chemotherapy, so that the most effective chemotherapy may be employed.

SUMMARY OF THE INVENTION

A method for predicting the effectiveness of an antineoplastic agent or combination of antineoplastic agents in an animal or human subject afflicted with a neoplastic disease is provided. The level of expression of at least one growth-regulated gene in neoplastic cells obtained from the subject is determined. Chemotherapy is initiated by administering the antineoplastic agent(s) to the subject. The level of expression of the growth-regulated gene is determined in neoplastic cells obtained from the subject subsequent to the administration of the antineoplastic agent(s), but prior to the beginning of neoplastic cell death, that is, preferably from about 6 to about 48 hours, and most preferably from about 24 to about 48 hours, after administration of the antineoplastic agent(s). The level of expression of the growth-regulated gene before and after administration of the antineoplastic agent(s) is compared. The presence or absence of a significant decrement in the level of expression of the gene has predicative value, indicating that continued therapy with the antineoplastic agent will-/will not likely induce remission. The invention is particularly useful in predicting the effectiveness of antineoplastic drugs in anti-leukemia therapy.

In a related invention, the neoplastic cells are incubated with the antineoplastic agent(s) in vitro. Accordingly, the level of expression of at least one growth-regulated gene in neoplastic cells obtained from the subject is determined. The cells are then incubated in vitro with the antineoplastic agent(s). The level of expression of the growth-regulated gene is determined again, prior to the beginning of neoplastic cell death, and compared to the level of expression before incubation of the cells with the antineoplastic agent(s). Preferably, the expression level of at least one non-cell cycle dependent gene is also determined, simultaneously with the determination of growth-regulated gene expression. Constancy of non-cell cycle dependent gene expression indicates that any observed decrement in growth-regulated gene expression due to the antineoplastic agent(s) is specific for the growth-regulated genes and not a consequence of a general inhibition of cellular mRNA or cytoreduction.

Gene expression may be conveniently determined by a variety of nucleic hybridization techniques effective for detecting specific RNA. Such methods are well known to those skilled in the art.

BRIEF DESCRIPTION OF THE FIGURES

FIG. 1 is a bar graph of the level of c-myc, histone H3, beta-actin and beta$_2$-microglobulin gene expression in acute myeloid leukemia patients before ("b") and 24 hours after ("a") initiation of chemotherapy.

FIG. 2 is a bar graph of the level of c-myc, H3, beta-actin and beta$_2$-microglobulin gene expression in acute lymphocytic leukemia patients before ("b") and 24 hours after ("a") initiation of chemotherapy.

DETAILED DESCRIPTION OF THE INVENTION

We have found that the success of a course of treatment with a particular antineoplastic (i.e., anticancer) agent(s) in treating neoplastic disease may be predicted on an individual patient basis by determining changes in the level of expression of certain genes in neoplastic cells of the patient as early as following the first administration of the drug. We have found that a decrease in the messenger RNA ("mRNA") levels of growth-regulated genes in neoplastic cells after a single dose of antineoplastic drug is predicative of complete remission, while lack of reduction in these mRNA's is predicative of a patient's eventual failure to achieve remission in response to the specified therapy. Indeed, we have found that detectable changes in the level of expression of growth-regulated genes occurs within hours following initiation of the course of chemotherapy. At the same time, the levels of expression of non-cell cycle dependent genes remain constant.

The test method of the present invention has particular utility in predicting the success of antineoplastic chemotherapy in any malignancy where growth-regulated genes are known to be over-expressed or highly expressed in comparison to normal tissue. Non-limiting examples include small cell carcinoma of the lungs; adenocarcinoma of the lung, breast, colon or prostate gland; testicular and ovarian carcinomas; and certain sarcomas, such as osteogenic sarcoma of the bone. In addition, the invention may be used in predicting the effectiveness of chemotherapy in the childhood tumors neuroblastoma and Wilm's tumor.

Leukemia is a neoplastic disease in which white corpuscle maturation is arrested at a primitive stage of cell development. The disease is characterized by an increased number of leukemic blast cells in the bone marrow, and by varying degrees of failure to produce normal hematopoietic cells. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukemia. In addition, leukemias with erythroid or megakaryocytic properties are considered myelogenous leukemias as well.

Chronic myelogenous leukemia (or chronic granulocytic leukemia) is characterized by abnormal proliferation of immature granulocytes—neutrophils, eosinophils, and basophils—in the blood, the bone marrow, the spleen, the liver, and sometimes in other tissues. A large portion of chronic myelogenous leukemia patients develop a transformation into a pattern indistinguishable from the acute form of the disease. This change is known as "blast crisis". The present invention is particularly useful in predicting the effectiveness of specific drugs in treating ALL and its known subtypes, AML and its known subtypes, and chronic myelogenous leukemia in blast crisis.

According to the practice of the invention, a sample of neoplastic cells are harvested from a patient afflicted with some form of neoplastic disease, which patient has not yet received any chemotherapy. The sampling occurs prior to the initiation of chemotherapy. For testing leukemia patients, bone marrow cells are a source of neoplastic cells, however, it is preferred to utilized peripheral blood leukocytes, owing to their ready availability through venipuncture. The level of expression of one or more growth-regulated genes in the neoplastic cells, that is, the relative number of mRNA transcripts of the gene in question, is determined for example, by any of a variety of nucleic acid hybridization techniques utilizing specific RNA or DNA probes for the target mRNA transcript.

By "growth-regulated gene" is meant a gene whose expression is linked to progression of the cell cycle and subsequent cell proliferation. Such genes are either not expressed, or expressed at low levels, in non-dividing (i.e., resting) cells. Growth-regulated genes may be preferentially expressed when $G_0$ cells are stimulated by growth factors. Identification of growth-regulated genes is generally accomplished by differential screening of cDNA. Methods for screening cDNA libraries to uncover growth-regulated genes are well-known to those skilled in the art. About 0.5–1.0% of the genes represented in a cDNA library are believed to be growth-regulated.

Many growth-regulated genes have been previously identified. All such genes behave similarly in that their expression is linked to the progression of the cell cycle and subsequent proliferation. However, some growth-regulated genes, such as the c-myc gene, are active throughout the cell cycle. Others are most active during specific phases of the cell cycle. For example, it is known that the histone H3 gene is most highly expressed during the S phase of the cell cycle. In addition, some growth-regulated functions or products appear to be interactive in inducing a transformed or neoplastic phenotype in previously normal cells. For example, the growth-regulated genes p53 and activated c-ras may interact in transforming previously normal primary embryonic cells.

Among the best studied growth-regulated genes are c-myc, Kelly et al., Cell 35:603–610 (1983); the various histone genes, Plumb et al., Nucleic Acids Res. 11:2391–2410 (1983); c-ras, Campisi et al., Cell 36:241–247 (1984); c-fos, Greenberg et al., Nature (Lond.) 311:433–438 (1984) and Cochran et al., Science 226:1080–1082 (1984); p53, Reich et al., Nature (Lond.) 308:199–201 (1984); c-myb, Torelli et al., Mol. Cell. Biol. 5:2874–2877 (1985); thymidine kinase, Liu et al., J. Biol. Chem. 260:3269–3275 (1985); calmodulin, Chafouleas et al., Cell 36:73–81 (1984) and ornithine decarboxylase, Kahana et al., Proc. Natl. Acad. Sci. USA 80:3645–3649 (1983). Other growth-regulated genes include 2A9 or kalcyclin, Calabretta et al., J. Biol. Chem. 261:12628–12632 (1986); 4F1 or vimentin, Ferrari et al., Mol. Cell. Biol. 6:3614–3620 (1986); and 2F1, which codes for an ATP/ADP translocase, Battini et al., J. Biol. Chem. 262:4355–4359 (1987). Genes for various proteases and protease inhibitors have also been identified as growth-regulated, Denhardt et al., Biochem. Biophys. Acta. 865:83–125 (1986); Edwards et al., Mol. Cell. Biol. 5:3280–3288 (1985). A growth-regulated gene coding for a member of the prolactin-growth hormone family has been identified by Lynzer et al., Proc. Natl. Acad. Sci. 81:4255–4259 (1984).

The c-myc and histone H3 genes are particularly useful in the practice of the present invention. Formerly known as mac, c-myc is the normal cellular counterpart of a viral gene believed to be the cause of avian myelocytomatosis. In the human genome, the gene exists as a 5.2 kb transcription unit composed of three exons of equal length. The first exon is believed to be non-coding. The function of the c-myc gene product is not known with certainty, but it is likely that it is related to the support of cell proliferation, perhaps by mediating the action of certain growth factors in the cell nucleus. Evidence for this association is myriad, but revolves principly around the observation that when cells are stimulated to proliferate by contact with growth factors, the activity of the c-myc gene increases rapidly and dramatically, always prior to the actual physical events associated with cell division. In addition, recent evidence suggests that increased activity of the c-myc gene may be associated with an inability of cells to complete their normal maturation program. Therefore, the c-myc gene may also play a role in regulating normal cell development.

Viral oncogenes, i.e., genes whose products have the ability to transform eukaryotic cells, have cellular counterparts, called proto-oncogenes. Their presence and expression within a cell may lead to a tumor phenotype. C-myc is one such proto-oncogene. In addition to c-myc, known growth-regulated proto-oncogenes include c-fos, c-Ha-ras, c-myb, and others. Histones are proteins which form the structural framework of chromatin by binding to DNA. Their synthesis is temporally associated with, or linked to, DNA synthesis in most eukaryotic cells. Histone H3 is a gene coding for one or four core histone proteins, namely H2A, H2B, H3 and H4. There are approximately 40 copies of each of the core histone genes per haploid genome of the human cell. Regulation of the expression of the histone gene appears to be complex, and dependent on both transcriptional, and post-transcriptional, mechanisms. Nevertheless, the histone genes, including H3, are most highly expressed during the S or DNA synthesis phase of the cell cycle.

The level of expression of the growth-regulated gene targeted for study is determined prior to chemotherapy by isolating total cellular RNA from the subjects's neoplastic cells and identifying mRNA transcripts of the target genes by hybridization techniques. Either complementary DNA (cDNA) or complementary RNA (cRNA) probes may be utilized for this purpose.

According to one method, total cellular RNA is purified from the neoplastic cells by homogenization in the presence of nucleic acid extraction buffer, followed by centrifugation. Nucleic acids are precipitated, and DNA is removed by treatment with DNase 1 and precipitation. The RNA molecules are then separated by gel electrophoresis on agarose gels according to standard techniques, and transferred to nitrocellulose filters by, e.g., the so-called "Northern" blotting technique. The RNA is immobilized on the filters by heating. Detection of specific RNA is accomplished using appropriately labelled DNA or RNA probes complementary to the RNA in question.

In addition to blotting techniques, the test may be carried out according to the technique of in situ hybridization. The latter technique is preferred since it requires fewer tumor cells. Also known as "cytological hybridization", the in situ technique involves depositing whole cells onto a microscope cover slip and probing the nucleic acid content of the cell with a solution containing radioactive or otherwise labelled cDNA or cRNA probes.

Example 1 illustrates the practice of the invention on nine AML patients (Table I) and nine ALL patients (Table II) utilizing peripheral blood as a source of neoplastic leukocytes, and radiolabelled cDNA probes and Northern blotting to detect DNA/RNA hybrids. The blotted RNA was first hybridized to c-myc and then histone H3 after removing residual hybridization. The expression levels of the growth-regulated genes c-myc and histone H3 (all patients), and the non-cell cycle dependent genes beta-actin (patients 1 through 6), and beta$_2$-microglobulin (patients 7 and 8), were determined from total RNA isolated from the patients immediately before therapy and 24 hours after administering the first course of antineoplastic drugs.

DNA probes complementary to the target mRNA may be obtained by extracting the relevant mRNA gene transcript and synthesizing cDNA by reverse transcription using reverse transcriptase. Alternatively, the probe may be obtained by cleaving the genome by endonuclear digestion and cloning the gene in question according to well-known techniques.

Appropriate DNA probes to various growth-regulated genes are well-known. Many such probes, such as the following probes listed in the American Type Culture Collection publication entitled *Human DNA Probes and Cloned Genes in the NIH Depository and Other ATCC Collections* (Feb. 20, 1988), are available from the ATCC: c-myc, 41010; c-myb, 41024; c-fos, 41042; c-Ha-ras, 41001. Many other DNA probes to growth-regulated genes are known and readily available.

The probe is suitably labeled with, e.g., a radionuclide such as $^{32}P$, $^{14}C$, or $^{35}S$; a heavy metal; or a ligand capable of functioning as a specific binding pair member for a labelled ligand, such as a labelled antibody, a fluorescent molecule, a chemolescent molecule, an enzyme or the like.

Probes may be labelled to high specific activity by either the nick translation method or Rigby et al., J. Mol. Biol. 113:237–251 (1977) or by the random priming method, Fienberg et al., Anal. Biochem. 132:6–13 (1983). The latter is the method of choice for synthesizing $^{32}P$-labelled probes of high specific activity from single-stranded DNA or from RNA templates. Both methods are well-known to those skilled in the art and will not be repeated herein. By replacing preexisting nucleotides with highly radioactive nucleotides, it is possible to prepare $^{32}P$-labelled DNA probes with a specific activity well in excess of $10^8$ cpm/microgram according to the nick translation method. Autoradiographic detection of hybridization may then be performed by exposing filters on photographic film. Densitometric scanning of the filters provides an accurate measurement of the mRNA transcript of the growth-regulated gene whose expression is determined.

Where radionuclide labelling is not practical, the random-primer method may be used to incorporate the dTTP analogue 5-(N-(N-biotinyl-epsilon-aminocaproyl)-3-aminoallyl)deoxyuridine triphosphate into the probe molecule. The thus biotinylated probe oligonucleotide can be detected by reaction with biotin binding proteins such as avidin, streptavidin, or anti-biotin antibodies coupled with fluorescent dyes or enzymes producing color reactions.

Representative antineoplastic (anticancer) agents, the effectiveness of which may be predicted in the individual patient according to the invention, may be categorized as follows according to The Pharmacological Basis of Therapeutic:

Alklating agents: Nitrogen mustards; ethylenimine derivatives such as triethylenethiophosphoramide (thio-tepa); and alkyl sulfonates such as busulfan;

Anti-Metabolites: Folic acid analogues such as methotrexate; pyrimidine analogues such as 5-fluorouracil and cytosine arabinoside; purine analogues such as 6-mercaptopurine and 6-thioguanine;

Natural products: Vinca alkaloids such as vinblastine and vincristine; antibiotics such as adriamycin and duanorubicin; and enzymes such as L-asparaginase;

Hormones: Adrenocorticosteroids such prednisone; progestins such as hydroxyprogesterone; androgens such as testosterone; estrogens such as diethylstilbestrol; and anti-estrogens such as tamoxifen;

Miscellaneous agents: Substituted ureas such as hydroxyurea; methylhydrazine derivatives such as procarbazine; adrenocortical suppressants such as mitotane; and substituted heavy metals such as cis-diaminedicholoroplatinum.

In particular, the effectiveness of the following antineoplastic agents, which find utility in antileukemic therapy, may be predicted according to the practice of the invention: mercaptopurine, methotrexate, cyclophosphamide, vincristine, thioguanine, daunomycin, epirubicin, ARA-C, cyclocythidine, M-AMASA, methylprednisolone, adriamacyn, prednisolone, idarubicin.

Cancer chemotherapy is typically administered in the form of multiple drug combinations or "combination chemotherapy". According to the present invention, the effectiveness of such drug combinations may be directly tested. Thus, reference in the appended claims to "antineoplastic agent" is intended to include combinations of antineoplastic agents.

Some drugs may be incompatible in a mixture due to different structures or charges. In such instances, the individual drugs of the combination could be tested on a solitary basis, and the results of the combined treatment inferred from the results on the individual drugs.

Shortly after the administration of the first dose of the selected antineoplastic drug or drugs, a second neoplastic cell sample is obtained from the subject, the cellular RNA is again isolated, and the probe-hybridization technique is repeated to assess the possible change in level in expression of the growth-regulated gene being monitored. The same amount of total RNA is exposed to hybridization as exposed in the pre-dosing hybridization. It is possible to observe a significant decrement in the expression of growth regulated genes shortly after the initiation of chemotherapy. Thus, the test provides a rapid method for predicting the effectiveness of a particular antineoplastic agent or combination of agents at the outset of a course of chemotherapy. The second antineoplastic cell sampling and growth-regulated gene expression determination should occur prior to the beginning of the generalized cell death which is associated with the progress of chemotherapy. Conditions of cell death give rise to a generalized reduction of cellular mRNA, which may be detected by decrements in the level of expression of non-growth regulated genes. The present invention, on the other hand, is directed to determining an early decrement in mRNA synthesis specific for growth-regulated genes at a time when the level of expression of other genes remains unaffected. Thus, the second sampling of neoplastic cells and determination of growth-regulated gene expression should take place before the onslaught of this generalized cell death. The second sampling occurs preferably from about 6 to about 48 hours, and most preferably from about 24 and 48 hours, after the first administration of the antineoplastic agent.

Comparison of the level of expression of the growth-regulated gene before and after the initiation of antineoplastic chemotherapy provides invaluable information to the treating physician. The absence of a significant decrement in the expression of the growth-regulated gene or genes under study signifies that more likely than not, the full course of therapy with the drug or drugs in question will not lead to remission. If the drug or drugs administered are observed to cause a significant decrement in the level of growth-regulated genes, it is likely that continuation of the full course of therapy will lead to eventual remission.

While changes in the level of a single growth-regulated gene may form the basis for predicting a patient's response to a particular antineoplastic agent or combination of agents, a more accurate determination of a drug's effectiveness may be achieved by following the expression of two or more growth-regulated genes. Decrements in expression two or more growth-regulated genes may be of greater prognostic value than a decrement in a single gene.

According to a preferred embodiment of the invention, the level of expression of one or more non-cell cycle dependent genes is determined simultaneously with the determination of the expression of growth-regulated genes. By "non-cell cycle dependent" gene is meant a gene whose level of expression is independent of cell cycle. Thus, these genes are expressed continuously in a steady state level. Many non-cell cycle genes are known. Such genes include, for example: gamma-actin, Gunning et al., Mol. Cell. Biol. 3:787–795 (1983); beta-actin, Ng et al., Mol. Cell. Biol. 5:2720–2732 (1985); beta$_2$-microglobulin, Kelly et al., Cell 35:603–610 (1983); glyceraldehyde-3-phosphate dehydrogenase ("GAPDH"), Dugaiczyk et al., Biochemistry 22:1605–1613 (1983); Olson et al., Mol. Cell Biol. 7:2104–2111 (1987).

Antineoplastic agents generally would not effect the mRNA levels of non-cell cycle dependent genes during the duration of the test of the present invention. Thus, non-cell cycle dependent gene expression is a useful control against non-specific variations in the target growth-regulated genes expression. The level of expression of one or more non-cell cycle dependent genes is thus preferably monitored according to the methods described herein. Expression of the non-cell cycle dependent genes beta-actin and beta$_2$-microglobulin is particularly useful in this regard. Beta-actin gene expression is abundant, and although growth factor-regulated, it is not cell-cycle dependent because its mRNA level is the same in quiescent and proliferating cells. Expression of beta$_2$-microglobulin is also abundant and equally expressed in all cells independently of the position in the cell cycle. Kelly et al., Cell 35:603–610 (1983).

While the invention as heretofore described contemplates monitoring the in vivo effect of selected chemotherapeutic agents on growth-regulated gene expression to predict remission, similar results of prognostic value may be obtained without actual drug administration to the patient, by incubating neoplastic cells from the subject in vitro with the desired chemotherapeutic agent or agents. The latter technique is particularly appropriate in neoplastic disease characterized by solid tumor masses.

According to this embodiment of the invention, a portion of a tumor is removed from the subject either at the time of surgical biopsy, or at the time of definitive surgery. The fresh tumor tissue is finely minced, and cultured in a suitable tissue culture medium. The total cellular RNA is isolated, and the level of expression of one or more growth-regulated genes is determined by hybridization, as described above. A second aliquot of the tumor tissue is treated in a similar manner except that following mincing of the tissue, the cells are cultured in a suitable culture medium containing one or more antineoplastic chemotherapeutic agents whose effectiveness in inducing remission in the subject is to be evaluated. The chemotherapeutic agent is added to the culture in an amount approximating the cellular concentration which would be experienced following in vivo administration of the agent to the subject. The tumor cells are incubated with the antineoplastic agent for a period of time sufficient for specific growth-regulated gene expression decrement to occur, but not long enough for generalized cell death to occur. Preferably, the incubation period lasts from about 6 to about 48 hours, 24 to 48 hours being most preferred. Most advantageously, the incubation period is about 24 hours. Following incubation, the hybridization assay is repeated using the same number of cells. The occurrence or lack of occurrence of decrement in the level of growth-regulated expression is predictive of eventual remission or lack of remission.

The practice of the invention is illustrated by the following non-limiting examples.

EXAMPLE 1

A. Patients

Patients with high peripheral white blood cell counts with at least 50% blast cells were selected (Tables I and II). Use of peripheral blood allowed repeated sampling without repeated marrow aspiration. Heparinized peripheral blood leukocytes were obtained by venipuncture before therapy and 24 hours after each patient received his/her first does of antineoplastic drugs. French-American-British classification of the leukemic cell populations was established by morphologic examination, and cytochemical reactions (PAS, sudan black, myeloperoxidase, chloroacetate esterase, nonspecific esterase). Cells were further characterized by surface phenotype (cALLa, Leu-1 antigen, DR, and a variety of anti-myeloid monoclonal antibodies), Tdt enzyme activity, and karyotype analysis. In patients with ALL, the rearrangement of the Ig locus was also analyzed. Permission for the use of human specimens was granted by the committee for Protection of "Human Subjects of the Children's Hospital of Philadelphia, Temple University, and the Department of Hematology of Modena University.

B. DNA Probes

The following probes were labelled by the nick translation method at high specific activity essentially according to the method of Rigby et al., J. Mol. Biol. 113:237-251 (1977) or by the random priming method of Feinberg et al., Anal. Biochem. 132:6-12 (1983): plasimids pMC415 and pMC413, carrying the 5'and 3'end of a c-myc gene probe (Dalla Favera et al., Proc. Natl. Acad. Sci. USA 79:6497-6501 (1982)); plasmid pFO 422 carrying a histone H3 gene; a human beta-actin cDNA (Gunning et al., Mol. Cell. Biol. 3:787-795 (1983)); and a human beta$_2$-microglobulin cDNA (Suggs et al., Proc. Natl. Acad. Sci. USA. 78:6613-6617 (1982)).

C. Nucleic Acids Isolation

Total cellular RNA was purified from leukemic cells according to Frazier et al., Mol. Cell. Biochem. 56:113-122 (1983). Briefly, the cells were homogenized in a Waring blender in extraction buffer (75 mM NaCl, 20 mM EDTA, 10 mM Tris-HCl, pH 8.0 and 0.2% sodium dodecyl sulfate ("SDS")), mixed 1:1 with buffer-saturated phenol. The aqueous phase was recovered by centrifugation and reextracted with an equal volume of phenol:chloroform:isoamyl alcohol (25:24:1), and then once again with chloroform:isoamyl alcohol (24:1). The nucleic acids were precipitated with ethanol. DNA was removed by treatment with DNase 1 and precipitated with 3M sodium acetate, pH 5.5. The integrity and amount of RNA in the samples were monitored by ethidium bromide staining of agarose-formaldehyde gels (see below). DNA extraction was performed essentially as described by Gross-Bellard et al., Eur. J. Biochem. 36:32-38 (1973).

D. Blotting

An agarose-formaldehyde gel was prepared by adding approximately 1.2 grams agarose, 10 ml 10X (i.e, 10-fold concentrated) 3-(N-morpholine)propanesulfonic acid ("MOPS"), and 87 ml diethylpyrocarbonate ("DEPC")-treated, autoclaved water to an autoclaved flask and dissolving the agarose by boiling. After cooling to 50° C., 5.1 ml of 37% formaldehyde was added to the gel, which was then cast in an 11×14 cm tray. The gel was given about one hour to polymerize. Ten to 300 micrograms of the above-obtained RNA is dissolved in 5 microliters of DEPC-treated, autoclaved water in a microcentrifuge tube. Twenty-five microliters of electrophoresis sample buffer (0.75 ml deionized formamide, 0.15 ml 10X MOPS, 0.24 ml formaldehyde, 0.1 ml deionized RNase-free water, 0.1 ml glycerol, 0.08 ml 10% (w/v) bromophenol blue) was then added and the solution heated to 65° C. for 15 minutes. One microliter of ethidium bromide solution (1.0 mg/ml) was then added to the sample, which was then mixed and loaded onto the gel. The gel was electrophoresed at about 30 V (constant voltage) for 18 hours. The gel was then prepared for transfer by soaking for two twenty-minute periods in 10X SSC (175.3 g NaCl, 88.2 g sodium citrate, in 1 liter final volume H$_2$O) at room temperature. The nitrocellulose filter to which the transfer was to take place was pre-soaked in distilled water for 5 minutes, followed by a 5 minute soak in 10X SSC. The filter was then layered over the gel and the RNA was transferred to the filter by capillary action. RNA was fixed to the nitrocellulose by baking for about 2 hours at 80° C. in vacuo.

E. Hybridization Procedure

Prehybridization of the nitrocellulose filters was carried out to reduce non-specific hybridization of probes to the filter. By incubating the filter for 30 minutes in 25 ml of 5X Denhardt's solution (0.9M NaCl, 50 mM phosphate buffer, 10 mM Tris, pH 8.0, 1 mM EDTA, 50% formamide, 1% bovine serum albumin ("BSA"), 1% polyvinylpyrrolidone ("PVP"), and 100 mg/ml of denatured salmon sperm DNA). The blotted RNA was hybridized with $^{32}$P-labelled probe (either c-myc, histone H3, beta-actin or beta$_2$-microglobulin probe; 10-50 mg of $^{32}$P-labelled DNA with a specific activity of at least 1.5-2×10$^7$ cpm) in the same buffer, to which is added 10% dextran sulfate. The latter accelerates the hybridization reaction, which is allowed to proceed for 20-24 hours at 42° C. Post hybridization washes were carried out to remove non-specifically bound probe. The washes were carried at 60° C., first in 1X SSC (0.5M NaCl, 0.015M sodium citrate) for 30 minutes, and then twice (30 minutes each time) in 0.1X SSC. Autoradiographic detection of hybrids was then performed by exposing the filters on Kodak X-ray film at −70° C. using intensifying screens, which were then developed according to the manufacturer's indications. Densitometric scanning of the filter was performed with the aid of a Zeineh-laser densitometer (Biomed Instruments, Inc. Fullertown Calif.). The accuracy and the linearity of the densitometer readings were tested by analyzing the X-ray films of the same Northern blots developed after different times of exposure.

TABLE I

Acute Myeloid Leukemia Patients and Therapy

| Patient | Age (Years) | FAB Type[1] | Therapy | | |
|---|---|---|---|---|---|
| 1 | 64 | $M_4$ | ARA-C | 150 | mg |
| | | | Thioguanine | 80 | mg |
| | | | Daunomycin | 40 | mg |
| | | | Methylprednisolone | 80 | mg |
| 2 | 17 | $M_3$ | Daunomycin | 40 | mg |
| | | | Methylprednisolone | 60 | mg |
| 3 | 55 | CML Myeloid BC | Epirubicin | 50 | mg |
| | | | ARA-C | 150 | mg |
| | | | Methylprednisolone | 80 | mg |
| 4 | 13 | $M_4$ | M-AMSA | 100 | mg |
| | | | Cyclocytidine | 1000 | mg |
| | | | Prednisolone | 80 | mg |
| 5 | 52 | $M_5$ | Vincristine | 2 | mg |
| | | | Epirubicin | 50 | mg |
| | | | ARA-C | 150 | mg |
| | | | Thioguanine | 160 | mg |
| 6 | 12 | $M_4$ | ARA-C | 100 | mg |
| | | | Daunomycin | 45 | mg |
| | | | Prednisone | 60 | mg |
| | | | Vincristine | 2 | mg |
| 7 | 28 | $M_3$ | Daunomycin | 40 | mg |
| | | | Methylprednisolone | 60 | mg |
| | | | ARA-C | 100 | mg |
| | | | Vincristine | 2 | mg |
| 8 | 40 | $M_2$ | Daunomycin | 40 | mg |
| | | | Prednisolone | 80 | mg |
| | | | ARA-C | 100 | mg |
| | | | Vincristine | 2 | mg |
| 9 | 48 | $M_2$ | Daunomycin | 40 | mg |
| | | | Methylprednisolone | 80 | mg |
| | | | ARA-C | 150 | mg |
| | | | Vincristine | 2 | mg |

[1]French-American-British type.

TABLE II

Acute Lymphocytic Leukemia Patients and Therapy

| Patient | Age (Years) | FAB Type | Therapy | | |
|---|---|---|---|---|---|
| 1 | 15 | $L_1$ | Vincristine | 2 | mg |
| | | | Epirubin | 60 | mg |
| | | | Methylprednisolone | 60 | mg |
| 2 | 9 | $L_1$ | Vincristine | 2 | mg |
| | | | Daunomycin | 40 | mg |
| | | | Presdnisolone | 100 | mg |
| 3 | 50 | CML Lymphoid BC | Vincristine | 2 | mg |
| | | | Daunomycin | 40 | mg |
| | | | Presdnisolone | 100 | mg |
| 4 | 40 | $L_1$ | Daunomycin | 40 | mg |
| | | | ARA-C | 150 | mg |
| | | | Methylprednisolone | 80 | mg |
| 5 | 62 | $L_1$ | Vincristine | 2 | mg |
| | | | Daunomycin | 40 | mg |
| | | | Prednisolone | 100 | mg |
| 6 | 16 | $L_1$ | Idarubicin | 15 | mg |
| 7 | 40 | $L_1$ | Vincristine | 2 | mg |
| | | | Daunomycin | 40 | mg |
| | | | Prednisolone | 100 | mg |
| 8 | 36 | ALL Ph+ | Vincristine | 2 | mg |
| | | | Adriamacyn | 80 | mg |
| | | | Methylprednisolone | 80 | mg |
| 9 | 12 | $L_1$ | Vincristine | 2 | mg |
| | | | Daunomycin | 40 | mg |
| | | | Methylprednisolone | 80 | mg |

One patient in each group (patient 3) was in the blast phase of chronic granulocytic leukemia. It may be noticed that the number of blast cells in the peripheral blood of the patients studied varied from 50% to 100%, but this variation would not be expected to significantly effect data on the mRNA levels of growth-regulated genes since the mRNA yield from mature leukocytes is much lower than from blast cells. Calabretta et al., Proc. Natl. Acad. Sci. USA 82:4463–4467 (1985). Table III lists the response to antineoplastic treatment for each patient at 24 hours and at the end of induction therapy. Hematological remission was defined as presence of less than 5% of blast cells in the bone marrow at the end of treatment.

TABLE III

Response to Therapy

| Patient Remission | Before Treatment | | 24 Hr Post Treatment | | Patient Remission |
|---|---|---|---|---|---|
| | WBC[1] | % blast | WBC | % blast | |
| Acute Myeloid Leukemia Patients | | | | | |
| 1 | 61,000 | 80 | 55,000 | 82 | — |
| 2 | 25,000 | 50 | 19,000 | 50 | — |
| 3 | 69,000 | 64 | 61,000 | 77 | — |
| 4 | 89,000 | 95 | 108,000 | 95 | — |
| 5 | 78,000 | 77 | 81,000 | 85 | + |
| 6 | 120,600 | 60 | 43,000 | 30 | + |
| 7 | 48,000 | 72 | 45,000 | 76 | — |
| 8 | 35,000 | 65 | 32,000 | 60 | + |
| 9 | 29,000 | 78 | 31,000 | 80 | — |
| Acute Lymphocytic Leukemia Patients | | | | | |
| 1 | 225,000 | 97 | 35,600 | 99 | + |
| 2 | 155,000 | 91 | 105,000 | 100 | + |
| 3 | 95,000 | 89 | 59,000 | 90 | + |
| 4 | 35,000 | 78 | 32,000 | 75 | partial[2] |
| 5 | 85,000 | 94 | 80,000 | 90 | + |
| 6 | 117,000 | 89 | 53,000 | 95 | — |
| 7 | 32,000 | 69 | 28,000 | 68 | partial[2] |
| 8 | 67,000 | 69 | 41,000 | 60 | — |
| 9 | 165,000 | 90 | 85,000 | 82 | + |

[1]White blood cells (leukocytes).
[2]10% blast cells were still present in the bone marrow at the end of treatment.

The mRNA levels of c-myc and histone H3 in nine patients with AML before and after therapy is shown in FIG. 1. The antineoplastic agents administered are listed in Table 1. In patients with AML, the therapy affects the mRNA levels of c-myc gene differentially. For example, in patients 1, 3, 4, 7 and 9, the mRNA levels of c-myc are essentially the same before and after therapy, whereas in patients 2, 5, 6 and 8, there is a significant decrease in the expression of c-myc mRNA. FIG. 1 also shows that the mRNA level of histone H3 is reduced by therapy in five patients (1, 2, 5, 6, and 8). In no patient, is the mRNA level of beta-actin or $beta_2$-microglobulin significantly modified by therapy.

The mRNA levels of c-myc and histone H3 in nine patients with ALL before and after therapy (Table II) is shown in FIG. 2. It is apparent that the expression of histone H3 is dramatically decreased in patients 1, 2, 5, 7 and 9, 24 hours after the first administration of antineoplastic drugs in comparison to pre-treatment levels. The mRNA level of the histone H3 gene is also moderately decreased in patient 3, while it is essentially unchanged or even increased in patients 4, 6 and 8. The expression of c-myc is drastically reduced by the therapy in patients 1, 2, 5 and 9, and is slightly reduced in patient 4. The c-myc mRNA level is unchanged after therapy in patients 3, 7 and 8, while it does increase in patient 6. Chemotherapy did not induced significant changes in the mRNA levels of beta-actin and $beta_2$-microglobulin genes.

Tables I and II show that except in ALL patient 1, the number of leukocytes as well as the percentage of blast cells were not significantly altered by the single does of antineoplastic drugs that the patients received. The absence of significant modifications in the percentage of blast cells indicates that the variations on the mRNA levels of growth-regulated genes after therapy are due to early effect of the antineoplastic drugs on the metabolic pathways necessary for the cell cycle progression of leukemic cells. Our studies also demonstrate that the first dose of chemotherapy induces early changes in the mRNA levels of the growth-regulated genes c-myc and H3 in approximately 65% of leukemic patients, while it does not effect the mRNA levels beta-actin and $beta_2$-microglobulin in any patient.

Without wishing to be bound by any theory, the reduction in the mRNA levels of c-myc and H3 after therapy might be the consequence of a direct effect on the transcription of growth-regulated genes in cycling cells. This interpretation is supported by the observation that a reduction of the mRNA levels of histone H3 can be observed, in some patients, as early as 6 hours after therapy. However, it is likely that the magnitude of the effect is increased by the short half-life of c-myc and H3 messages as compared to the much longer half-life of beta-actin. Independent of the mechanism involved, these studies indicate that early variations in the mRNA levels of growth-regulated genes, as compared to unchanged levels of non-cell cycle genes beta-actin and $beta_2$-microglobulin, are due to a specific effect rather than being the result of a general inhibition of cellular RNA metabolism.

A decrease in the mRNA level of histone H3 measured 24 hours after a single dose of chemotherapy was observed in five AML patients (1, 2, 5, 6 and 8), whereas c-myc mRNA level was decreased in four of these patients (2, 5, 6 and 8). Hematologic remission was obtained in patients 5, 6 and 8. Levels of H3 mRNA were decreased by the therapy in six (1, 2, 3, 5, 7 and 9) out of nine ALL patients. The expression of c-myc was decreased in four (1, 2, 5 and 9) of these six ALL patients. Five ALL patients (1, 2, 3, 5 and 9) were in complete remission at the end of the chemotherapy. Partial remissions were obtained in patient 4, in whom 24 hours after therapy only the expression of c-myc was reduced, and in patient 7, in whom 24 hours after therapy only the expression of H3 was reduced.

These results indicate that lack of a concomitant reduction of two growth-regulated genes c-myc and histone H3, is unfavorable prognostic factor. None of the six patients with no changes or increases of c-myc and histone H3 mRNA levels after therapy achieved remission. Our findings also indicate that a decrease in the mRNA levels of c-myc or histone H3 24 hours after administration of single dose of chemotherapy is predicative of eventual obtainment of complete hematologic remission.

The following example is illustrative of the practice of the invention utilizing an in situ hybridization technique.

EXAMPLE 2 A. Tissue Preparation

Tumor tissue, either at the time of surgical biopsy or at the time of definitive surgery, is removed from the patient and minced into fine pieces which are immediately placed into sterile 25 cm² tissue culture flasks containing either (i) fresh tissue culture medium alone (RPMI 1640) supplemented with one ml of L-glutamine, 1 ml of sodium pyruvate, 1 ml of non-essential amino acids, 0.8 ml of $NaHCO_3$, 0.75 ml of penicillin/streptomycin solution per 100 ml of medium, and 5% (v/v fetal calf serum), or (ii) the same medium containing the antineoplastic agent(s) of interest at a final concentration approximating the cellular concentration expected after in vivo administration of the agent(s) to a patient. After 24 hours incubation at 37° C. in an atmosphere containing 5% $CO_2$, the tissue is immediately frozen in OCT tissue embedding medium (Tissue Tek II, Miles Laboratories) in liquid nitrogen. Specimens can be stored indefinitely under these conditions. The frozen tissue block is placed in a $-20°$ C. cryostat chamber for thirty minutes to equilibrate the block's temperature with the temperature of a microtome knife ($-20°$ C.) with which tissue sections (about 4–20 microns thick) are cut. Glass slides are pre-treated by incubating them at 65° C. for 3 hours in Denhardt's solution (0.02% Ficol L, 0.02% PVP, 0.02% BSA) containing 450 mM NaCl/45 mM sodium citrate (pH 7.0). The slides are rinsed in double-distilled water and fixed for 20 minutes in ethanol:acetic acid (3:1). Cut sections are floated onto the pre-treated glass slides and then smoothed and flattened on the slides with a soft bristle brush. The slides are then warmed to 50° C. on a hot plate for 2 minutes, and air dried. Next, the slides are fixed in 4% paraformaldehyde for 20–30 minutes at room temperature, rinsed for 5 minutes in 3X phosphate-buffered saline ("PBS"), and then rinsed twice (5 minutes each) in 1X PBS. Treated tissues are then dehydrated by 5 minute emersions in graded ethanol solutions (30%, 60%, 80%, 95%, 100%). The slides are then air dried, and stored indefinitely at $-20°$ C.

B. Pre-Hybridization Treatment

The above-prepared slides are rinsed by dunking 4–5 times in DEPC-treated water. The slides are rehydrated for 10 minutes in PBS containing 5 mM $MgCl_2$. Next, the slides are transferred to 0.1M freshly-prepared triethanolamine (3.71 g/200 ml water) for 5 minutes, and then transferred to 0.1M freshly-prepared triethanolamine, 0.25% (v/v) acetic anhydride (200 ml triethanolamine+0.5 ml acetic anhydride) for 5 minutes. The slides are then rinsed in PBS, 5 mM $MgCl_2$. At this point, the slides may be divided into two sets, one set is utilized as an RNase control. The remaining slides are kept in PBS, 5 mM $MgCl_2$. The remaining cells are treated with RNase A (Sigma, St. Louis, Mo.) in RNase buffer (20 ml of 10 mg/ml DNase-free RNase A stock solution, added to 1 ml of 0.5M NaCl, 10 mM Tris-HCl, pH 8.0, 1 mM EDTA, final concentration: 200 mg/ml). The RNase A-containing buffer solution is prewarmed to 37° C., layered over the cells, and incubated for 30 minutes at 37° C. Thereafter, the slides are rinsed twice in PBS, 5 mM $MgCl_2$. The slides are then transferred to 0.2M Tris-HCl, 0.1M glycine (750 mg/100 ml) pH 7.4, for 10 minutes. The slides are rinsed in 2X SSC (20X=3M NaCl, 0.3M sodium citrate, pH 7.2) and transferred to 2X SSC, 50% formamide, which is prepared by adding 100 ml formamide to 80 ml of DEPC-treated water and 20 ml 20X SSC (90 ml:90 ml:20 ml). (50% formamide is used where hybridization is to radiolabelled probes; where hybridization is with biotinylated probes, 45% formamide is employed.) The solution is heated to 65° C. for 10 minutes just prior to hybridization. At this time, the probe is prepared for use in the hybridization step.

C. Preparation Of Labeled Probe Solution (i) $^3H$ or $^{35}S$-Labelled Probes

Lyophilized radiolabelled probe is melted in Hybridization Cocktail (Amresco, Solon Ohio) containing 50% formamide at room temperature. The final concentration of the labelled probe should be about 200–500 ng/ml of the hybridization cocktail. Once prepared, the probe-cocktail solution may be stored indefinitely at −20° C. The probe-cocktail should be heated in a microcentrifuge tube to about 95° C. in a heating block for about 10 minutes prior to use in the hybridization procedure.

(ii) Biotin-Labelled Probes

Lyophilized biotin-labelled probe is melted in Hybridization Cocktail containing 45% formamide, prepared by mixing 0.9 ml of 50% formamide cocktail with 0.1 ml of 0% formamide cocktail. The final concentration of the labelled probe in the hybridization cocktail should be about 200–500 ng/ml of hybridization cocktail. Once prepared, the probe-cocktail solution may be stored indefinitely at −20° C. Prior to use in the hybridization procedure, the probe-cocktail should be heated in an microcentrifuge tube to about 95° C. in a heating block for about 10 minutes.

D. Hybridization

About 30 ml of hot hybridization cocktail containing labelled probe is placed on the slide-mounted specimen, being certain that all liquid is removed from the slide, except in a small area which contains the tumor cells. The slide is covered with a second slide, parafilm (4 squares, 2-side-by-side), clipped together and transferred to a 37° C. humidified slide warmer, or to a covered water bath. Hybridization is allowed to proceed overnight.

E. Hybridization Washing

The dilutions specified herein are all made in DEPC-treated water.

The hybridized slides are washed in seven separate washing steps as follows. If biotinylated rather than radiolabelled probes are employed, a 50% formamide, 2X SSC solution is used for Wash #1 (90 ml formamide, 20 ml 20X SSC, 90 ml DEPC-treated H$_2$O), and a 50% formamide 1X SSC solution is used for Wash #3 (90 ml formamide, 10 ml 20X SSC, 100 ml DEPC-treated H$_2$O).

Wash #1: 50% formamide, 2X SSC for 30 minutes at 37° C.

Wash #2: 50% formamide, 1X SSC for 30 minutes at 37° C.

Wash #3: 0.2X SSC, 0.1% SDS (5 ml of 20X SSC, 500 mg SDS qs to 500 ml) for 3 minutes at room temperature.

Wash #4: Repeat Wash #3.

Wash #5: 0.16X SSC, 0.1% SDS (4 ml of 20X SSC, 500 mg SDS, qs to 500 ml) for 3 minutes at room temperature.

Wash #6: Repeat Wash #5.

Wash #7: 2X SSC, 0.1% SDS for 1 minute at room temperature.

The cells are then incubated in Tris-saline (0.1M Tris-HCl 0.1M NaCl, pH 7.5) with 3% BSA for 5 minutes by gently layering the solution over the cells on the slide. The slides are then air dried.

F. Hybrid Signal Detection (biotinylated DNA probes)

The following procedure illustrates the detection of hybridization of target mRNA transcripts to biotinylated cDNA probes. These buffers are prepared:

Buffer #1: 0.1M Tris-HCl (pH 7.5), 0.1M NaCl, 2 mM MgCl$_2$, 0.05% (v/v) Triton [1.58 g/100 ml; 0.584 g/100 ml; 0.019 g/100 ml; 0.050 ml/100 ml); Buffer #2: Buffer #1 with 3% (w/v=3 g/100 ml) BSA; Buffer #3: 0.1M Tris-HCl (pH 9.5), 0.1M NaCl, 50 mM MgCl$_2$ (1.58 g/100 ml; 0.584 g/100 ml; 0.48 g/100 ml).

The dried slides are rehydrated in Buffer #1 for 10 minutes, then a solution of 2 ml of streptavidin stock solution (1 mg/ml per 1 ml of Buffer #1, final concentration=2 mg/ml) is layered over the slides. The slides are then covered with a parafilm square, and incubated for 10 minutes. The slides are then washed with at least 20–40 volumes of Buffer #1 for about 3 minutes. The washing procedure is repeated 3 times. One microliter of alkaline phosphatase (1 mg/ml, Bethesda Research Laboratories, Bethesda, Md.) is mixed with 1 ml of Buffer #1 to yield an alkaline phosphatase solution having a final concentration of 1 microgram/ml. This solution is layered over the slide, which is covered with a parafilm square and incubated for 10 minutes. The slides are then washed again in at least 20–40 volumes of Buffer #1 for about 3 minutes. The washing is repeated. The slides are then washed with Buffer #3 for 3 minutes. The washing is repeated once. 8.8 microliters of nitroblue tetrazoleum solution (Bethesda Research Laboratories) and 6.6 microliters of 5-bromo-4-chloro-3-indolyl phosphate solution (Bethesda Research Laboratories) are mixed into 2 ml of Buffer #3. The solution is laid onto the slides, which are covered with parafilm to prevent evaporation. The slides are incubated in the dark to maximum development time of 4 hours. Ideally, the slides are incubated in a covered 37° C. water bath. The slides are then washed in 20 mM Tris (pH 7.5), 5 mM EDTA to terminate the color reaction. The slides are rinsed in 95% ethanol for about 5 to 10 seconds and then rinsed in 100% ethanol for another 5 to 10 seconds. The slides are placed in xylene for 5 to 10 seconds and then mounted, e.g. in "PERMOUNT" (Fisher Chemical). The cells and dye are stable if stored in a light-type box. The extent of hybrid formation is quantitated by appropriate densitometry.

As an alternative to the above tissue preparation of Example 2, the tumor tissue is removed from the patient and immediately frozen in liquid N$_2$ and cut in sections of varying degrees of thickness (50–100 microns). The sections are then thawed in either (i) fresh tissue culture medium or (ii) the same medium, further containing the antineoplastic agent(s) of interest in accordance with Example 2, A. Tissue Preparation, above. After 24 hours incubation, the tissue slices are refrozen and sliced into thinner sections (about 4–20 microns thick), and the balance of the procedure of Example 2 is followed.

While the method of the present invention is illustrated by RNA/DNA hybridization, that is by using DNA probes to detect mRNA transcripts of the target growth-regulated and non-cell cycle dependent genes, detection is also possible by means of a RNA/RNA hybridization technique, utilizing RNA probes having nucleotide sequences complementary to the target mRNA transcripts.

The present invention may be embodied in other specific forms without departing from the spirit or essential attributes thereof and, accordingly, reference should be made to the appended claims, rather than to the foregoing specification, as indicating the scope of the invention.

We claim:

1. A method for screening antineoplastic agents as candidates for treatment of a neoplastic disease in a human subject characterized by elevated expression of a growth-regulated proto-oncogene, comprising the following steps:

(a) determining the level of transcripts of the growth-regulated proto-oncogene in neoplastic cells of the subject prior to the first administration of a candidate antineoplastic agent to the subject;

(b) administering the antineoplastic agent to the subject;

(c) determining the level of transcripts of the growth-regulated gene in neoplastic cells obtained from the subject up to about 48 hours after the first administration of the antineoplastic agent; and (d) comparing the transcript level of the growth-regulated gene as determined in (a) with the transcript level of the gene as determined in (c), a decrement in the transcript level of the growth-regulated gene indicating that the antineoplastic agent will likely be effective in inducing remission of neoplastic disease in the subject.

2. A method according to claim 1 comprising the additional steps of:

determining the transcript level of at least one non-cell cycle dependent gene in neoplastic cells of the subject prior to the first administration of the antineoplastic agent to the subject;

determining the transcript level of the non-cell cycle dependent gene in neoplastic cells obtained from the subject up to about 48 hours after the first administration of the antineoplastic agent; and comparing the transcript level of the non-cell cycle dependent gene before and after administration of the antineoplastic agent.

3. A method according to claim 2 wherein the non-cell cycle dependent gene is selected from the group consisting of beta-actin and beta$_2$-microglobulin.

4. A method according to claim 1 wherein the transcript level of the growth-regulated gene in (c) is determined from about 6 to about 48 hours after administration of the antineoplastic agent.

5. A method according to claim 4 wherein the transcript level of the growth-regulated gene in (c) is determined from about 24 to about 48 hours after administration of the antineoplastic agent.

6. A method according to claim 1 wherein the transcript level of the growth-regulated gene is determined by RNA/DNA hybridization or RNA/RNA hybridization.

7. A method according to claim 6 wherein the hybridization comprises in situ hybridization.

8. A method according to claim 1, 2 or 6 wherein the growth-regulated gene comprises is c-myc.

9. A method according to claim 8 wherein the neoplastic disease comprises leukemia.

10. A method for screening antineoplastic agents as candidates for treatment of a neoplastic disease in a human subject characterized by elevated expression of a growth-regulated proto-oncogene, the steps comprising:

(a) determining the level of transcripts of the growth-regulated proto-oncogene in neoplastic cells obtained from the subject;

(b) incubating the neoplastic cells in vitro for a period of time with a candidate antineoplastic agent;

(c) determining the level of transcripts of the growth-regulated gene in the neoplastic cells following incubation of the cells with the antineoplastic agent for up to about 48 hours; and (d) comparing the transcript level of the growth-regulated gene as determined in (a) with the transcript level of the gene as determined in (c), a decrement in the transcript level of the growth-regulated gene indicating that the antineoplastic agent will likely be effective in inducing remission of neoplastic disease in the subject.

11. A method according to claim 10 comprising the further steps of:

determining the transcript level of at least one non-cell cycle dependent gene in the neoplastic cells obtained from the subject in (a);

determining the transcript level of the non-cell cycle dependent gene in the neoplastic cells following incubation of the cells with the antineoplastic agent for up to about 48 hours; and comparing the transcript level of the non-cell cycle dependent gene before and after incubation of the neoplastic cells with the antineoplastic agent.

12. A method according to claim 10 wherein the period of incubation in (b) is from about 6 to about 48 hours.

13. A method according to claim 12 wherein the period of incubation is from about 24 to about 48 hours.

14. A method according to claim 10 wherein the transcript level of the growth-regulated gene is determined by RNA/DNA hybridization or RNA/RNA hybridization.

15. A method according to claim 14 wherein the hybridization comprises in situ hybridization.

16. A method according to claim 10, 11 or 14 wherein the growth-regulated gene is c-myc.

17. A method according to claim 1 wherein the neoplastic disease is leukemia.

18. A method according to claim 17 wherein the neoplastic disease is acute lymphocytic leukemia.

19. A method according to claim 17 wherein the neoplastic disease is acute myelocytic leukemia.

20. A method according to claim 10 wherein the neoplastic disease is leukemia.

21. A method according to claim 20 wherein the neoplastic disease is acute lymphocytic leukemia.

22. A method according to claim 20 wherein the neoplastic disease is acute myelocytic leukemia.

* * * * *